(12) United States Patent
Hahn et al.

(10) Patent No.: US 8,474,977 B2
(45) Date of Patent: Jul. 2, 2013

(54) FIXED OPTICAL SYSTEM HAVING AN ADJUSTABLE TARGET

(75) Inventors: Andrew M. Hahn, Anaheim, CA (US); Michael M. Martin, Newport Beach, CA (US); Argelio M. Olivera, Mission Viejo, CA (US); Michael J. Papac, Tustin, CA (US); Ronald T. Smith, Irvine, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 190 days.

(21) Appl. No.: 12/860,011

(22) Filed: Aug. 20, 2010

(65) Prior Publication Data

US 2011/0043760 A1   Feb. 24, 2011

Related U.S. Application Data (60) Provisional application No. 61/235,800, filed on Aug. 21, 2009.

(51) Int. Cl.
*A61B 3/10* (2006.01)
*A61B 18/18* (2006.01)
*G02B 21/26* (2006.01)

(52) U.S. Cl.
USPC .............. 351/221; 351/245; 606/15; 359/393

(58) Field of Classification Search
USPC ....... 351/221, 244, 245; 606/15, 16; 359/384, 359/385
See application file for complete search history.

(56) References Cited

U.S. PATENT DOCUMENTS

| | | | | |
|---|---|---|---|---|
| 3,758,217 | A * | 9/1973 | Stokstad | 356/256 |
| 5,539,422 | A | 7/1996 | Heacock et al. | |
| 6,571,041 | B2 * | 5/2003 | Bourcier et al. | 385/52 |
| 7,518,097 | B2 * | 4/2009 | Ashley et al. | 250/216 |
| 2005/0225725 | A1 | 10/2005 | Warden et al. | |
| 2006/0146425 | A1 * | 7/2006 | Zimmermann | 359/819 |
| 2006/0215966 | A1 | 9/2006 | Nagano et al. | |
| 2007/0091411 | A1 | 4/2007 | Mori et al. | |
| 2008/0285002 | A1 * | 11/2008 | Rief | 355/67 |
| 2010/0102248 | A1 * | 4/2010 | Milas et al. | 250/440.11 |

FOREIGN PATENT DOCUMENTS

EP   0179426   4/1986

OTHER PUBLICATIONS

European Extended Search Report for EP 10810630.3 with mailing date Nov. 26, 2012, 7 pages.

* cited by examiner

*Primary Examiner* — Jordan Schwartz (57) ABSTRACT

A fiber optic illuminator is provided comprising an optics bed, a light source, a collimating lens, and a condensing lens. The light source is mounted in a fixed position with respect to the optics bed. The collimating lens is mounted in a fixed position with respect to the optics bed and collimates at least a portion of the light from the light source. A condensing lens receives the substantially collimated light output and focuses the collimated light output to optically couple to an optical fiber. The condensing lens may be mounted on an adjustable mount. The tolerances of the fixed optical elements i.e. light source and collimating lens allow the fixed optical elements to be positioned with a minimal amount of variation where the variation is determined by manufacturing tolerances associated with these individual elements and their mounts and couple them to the optics bed.

6 Claims, 12 Drawing Sheets

FIXED OPTICAL SYSTEM HAVING AN ADJUSTABLE TARGET

This application claims priority to U.S. Provisional Application Ser. No. 61/235,800 filed on Aug. 21, 2009.

TECHNICAL FIELD OF THE INVENTION

The present disclosure relates to tools for use in ophthalmic surgery and more particularly to aligning optical components of ophthalmic surgical equipment.

BACKGROUND OF THE INVENTION

Anatomically, the eye is divided into two distinct parts—the anterior segment and the posterior segment. The anterior segment includes the lens and extends from the outermost layer of the cornea (the corneal endothelium) to the posterior of the lens capsule. The posterior segment includes the portion of the eye behind the lens capsule. The posterior segment extends from the anterior hyaloid face to the retina, with which the posterior hyaloid face of the vitreous body is in direct contact. The posterior segment is much larger than the anterior segment.

The posterior segment includes the vitreous body—a clear, colorless, gel-like substance. It makes up approximately two-thirds of the eye's volume, giving it form and shape before birth. It is composed of 1% collagen and sodium hyaluronate and 99% water. The anterior boundary of the vitreous body is the anterior hyaloid face, which touches the posterior capsule of the lens, while the posterior hyaloid face forms its posterior boundary, and is in contact with the retina. The vitreous body is not free-flowing like the aqueous humor and has normal anatomic attachment sites. One of these sites is the vitreous base, which is a 3-4 mm wide band that overlies the ora serrata. The optic nerve head, macula lutea, and vascular arcade are also sites of attachment. The vitreous body's major functions are to hold the retina in place, maintain the integrity and shape of the globe, absorb shock due to movement, and to give support for the lens posteriorly. In contrast to aqueous humor, the vitreous body is not continuously replaced. The vitreous body becomes more fluid with age in a process known as syneresis. Syneresis results in shrinkage of the vitreous body, which can exert pressure or traction on its normal attachment sites. If enough traction is applied, the vitreous body may pull itself from its retinal attachment and create a retinal tear or hole.

Various surgical procedures, called vitreo-retinal procedures, are commonly performed in the posterior segment of the eye. Vitreo-retinal procedures are appropriate to treat many serious conditions of the posterior segment. Vitreo-retinal procedures treat conditions such as age-related macular degeneration (AMD), diabetic retinopathy and diabetic vitreous hemorrhage, macular hole, retinal detachment, epiretinal membrane, CMV retinitis, and many other ophthalmic conditions.

A surgeon performs vitreo-retinal procedures with optical tools that include a number of optical components. For example, a microscope and special lenses designed to provide a clear image of the posterior segment may be one of these tools. Surgeons often use several microsurgical instruments inserted through the incisions such as a fiber optic light source to illuminate inside the eye, an infusion line to maintain the eye's shape during surgery, and instruments to cut and remove the vitreous body.

During such surgical procedures, proper illumination of the inside of the eye is important. Typically, a thin optical fiber is inserted into the eye to provide the illumination. A light source, such as a metal halide lamp, a halogen lamp, a xenon lamp, or a mercury vapor lamp, is often used to produce the light carried by the optical fiber into the eye. The light passes through several optical elements (typically lenses, mirrors, and attenuators) and is launched at the optical fiber that carries the light into the eye. The quality of this light is dependent on several factors including the alignment of the various optical elements selected.

SUMMARY OF THE INVENTION

The present disclosure provides an ophthalmic endoilluminator that substantially eliminates or reduces disadvantages and problems associated with previously developed systems. More specifically, the present disclosure provides an ophthalmic endoilluminator light source that fiber couples to an ophthalmic endoilluminator fiber to illuminate interior regions of the eye.

In one embodiment a fixed optical system is provided. This fixed optical system includes a number of fixed optical elements, an optics bed, and one or more optical targets. The fixed optical elements are mounted in fixed positions with respect to the optics bed. By fixing the location of each optical element and allowing those elements only to vary within manufacturing tolerances of their location the overall potential for misalignment of the overall optical system is reduced. This allows the entire system to be adjusted with an optical target mounted on an adjustable mount wherein the adjustable mount allows the optical target to translate along one or more axes and rotate about the one or more axes.

Another embodiment of the present invention provides a fiber optic illuminator. This fiber optic illuminator includes a number of fixed optical elements, an optics bed, and one or more optical targets. The optical elements are mounted in fixed positions with respect to the optics bed wherein those positions are fixed within manufacturing tolerances of the mounts on the optic bed. The optical target may be a port or an optical assembly that couples to an optical port that accepts an optical fiber. An adjustable mount on which the port is mounted may translate along one or more axes and rotate about the one or more axes.

Yet another embodiment of the present disclosure provides a fiber optic illuminator. This fiber optic illuminator includes at a minimum an optics bed, a light source, a collimating lens, and a condensing lens. The light source is mounted in a fixed position with respect to the optics bed. The light source produces light. The collimating lens which is also mounted in a fixed position with respect to the optics bed substantially collimates at least a portion of the light output of the light source. A condensing lens receives the substantially collimated light output and focuses or condenses the collimated light output so that it may be optically coupled to an optical fiber. The condensing lens may be mounted on an adjustable mount. This adjustable mount may allow the condensing lens to translate along one or more axes and rotate about the one or more axes. The tolerances of the fixed optical elements i.e. light source and collimating lens allow the fixed optical elements to be positioned with a minimal amount of variation where the variation is determined by manufacturing tolerances associated with these individual elements and their mounts and couple them to the optics bed.

Additionally the fiber optic illuminator may include a control system wherein servos or other mechanisms are used to adjust the adjustable mount. The control system may direct these adjustments. In one embodiment, a thermistor physically coupled to the optics bed provides an input to the control system that allows the control system to direct adjustments of the adjustable mount based on changes within the fiber optic illuminator detected through the use of the thermistor. The optics bed may be manufactured integrally from a single block of material. This optics bed may include various components such as the base plate, optical element brackets and an optical block. Other embodiments may use individual components manufactured to relatively tight tolerances with small tolerances to be physically coupled to the base plate.

Still another embodiment provides a method of generating an input to a fiber optic or optical fiber. This method involves first generating light with a light source wherein the light source is fixed to an optics bed. A collimating lens which is also fixed to the optics bed substantially collimates the light. The light is then provided to a condensing lens wherein the condensing lens focuses or optically couples the substantially collimated light to an optical port operable to receive an optical fiber. The condensing lens may be adjustably mounted to the optics bed. This may be done so with an adjustable mount wherein the mount allows the condensing lens to translate and rotate about one or more axes.

BRIEF DESCRIPTION OF THE DRAWINGS

For a more complete understanding of the present disclosure and the advantages thereof, reference is now made to the following description taken in conjunction with the accompanying drawings in which like reference numerals indicate like features and wherein.

DESCRIPTION OF THE INVENTION

Preferred embodiments of the present disclosure are illustrated in the FIGs., like numerals being used to refer to like and corresponding parts of the various drawings.

Embodiments of the present disclosure substantially address problems associated with illuminating the interior of the eye. More specifically, a fiber optic illuminator is provided. This fiber optic illuminator includes at a minimum an optics bed, a light source, a collimating lens, and a condensing lens. The light source is mounted in a fixed position with respect to the optics bed. The light source produces light. The collimating lens which is also mounted in a fixed position with respect to the optics bed substantially collimates at least a portion of the light output of the light source. A condensing lens receives the substantially collimated light output and focuses or condenses the collimated light output so that it may be optically coupled to an optical fiber. The condensing lens may be mounted on an adjustable mount. This adjustable mount may allow the condensing lens to translate along one or more axes and rotate about the one or more axes. The tolerances of the fixed optical elements i.e. light source and collimating lens allow the fixed optical elements to be positioned with a minimal amount of variation where the variation is determined by manufacturing tolerances associated with these individual elements and their mounts and couple them to the optics bed.

Fiber optic illuminator optical trains have traditionally been designed so that each optical component is adjustable in at least one axis to allow for alignment of the system for maximum output. The problem with this approach is that each element must be aligned serially around several axes. This results in a compounding multitude of alignments that must be performed in sequence to achieve an aligned system. For example if the following 5 elements; Light source, Collimating Lens Image Reflector, Cold mirror, and Condensing lens, all had to be adjusted in 5 axes (X, Y, Z, Theta X, Theta Y), there would be 25 adjustments that would be made to align a single optical path. Each of these adjustable systems would require a multitude of expensive mechanical parts that would take a large amount of time to assemble. Furthermore a misalignments or compounding misalignments could impact downstream alignments to the point they exceed the limits of travel of the mechanisms. Additionally from a reliability standpoint having this large number of variables increases the odds of a future misalignment in the field.

In embodiments of the present disclosure, an optical train for a fiber optic Illuminator is provided where the key optical elements are held in a fixed position, by tightly tolerance machined parts whose nominal dimensions result in an aligned system. Any variation in the location of the components and the resulting optical beam due to normal manufacturing variation would be compensated for by adjusting the position of the target. In one embodiment the target is the condensing lens and the port which accepts an incoming fiber. In one embodiment, this Lens—Port assembly is adjustable for translation in 2 directions and in rotation around each of the translation axes. This allows the entire optical train be aligned by adjusting a single assembly at a single location with only adjustments in 4 directions.

Figure 1:
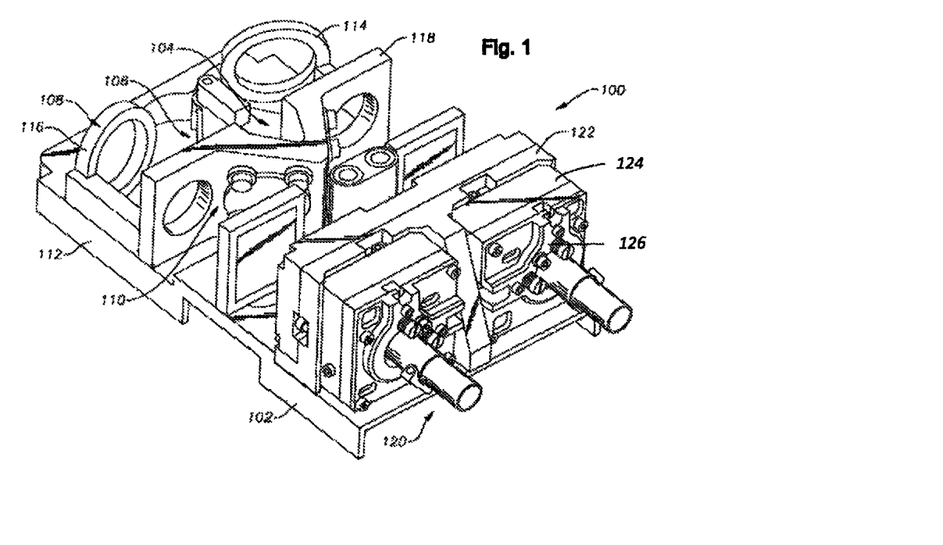
FIG. 1 provides the basic construction of a fiber optic illuminator with a fixed optical system in accordance with embodiments of the present invention.

FIG. 1 provides the basic construction of a fiber optic illuminator 100 with a fixed optical system in accordance with embodiments of the present invention. This FIG. shows the basic construction of a Fiber Optic Illuminator with a fixed optical system, with adjustable target. In this case the target is the Condensing lens—Output Port Assembly. The other components of the assembly that are fixed are the light Source, The Collimating Lens, Reflector, and Cold Mirror. The Condensing Lens—Output Port Assembly is adjustable in Horizontal and Vertical translation and in Rotation about the two translation axes. Each mechanism has a means to lockdown motion once the desired position is reached.

Fiber optic illuminator 100 includes a number of fixed optical elements, an optics bed 102, and an adjustable optical target. The fixed optical elements may include a fixed light source 104 (such as a bulb), a collimating lens 106, a cold mirror 108, and a reflector 110 which are all mounted in fixed positions having tight tolerances to the optics bed 102. Furthermore, optics bed 102 may include a base plate 112, optical element brackets 114 and 116, and an optical block 118. The optical element brackets may hold the various individual fixed optical elements 104, 106, 108, and 110. Adjustable mount 122 mechanically couples to optical target/condensing lens 124 and optical port 126. The adjustable mount 122 allows the adjustable target/(condensing lens/fiber optic port 120) to translate about one or more axes and rotate about these axes.

Figure 2:
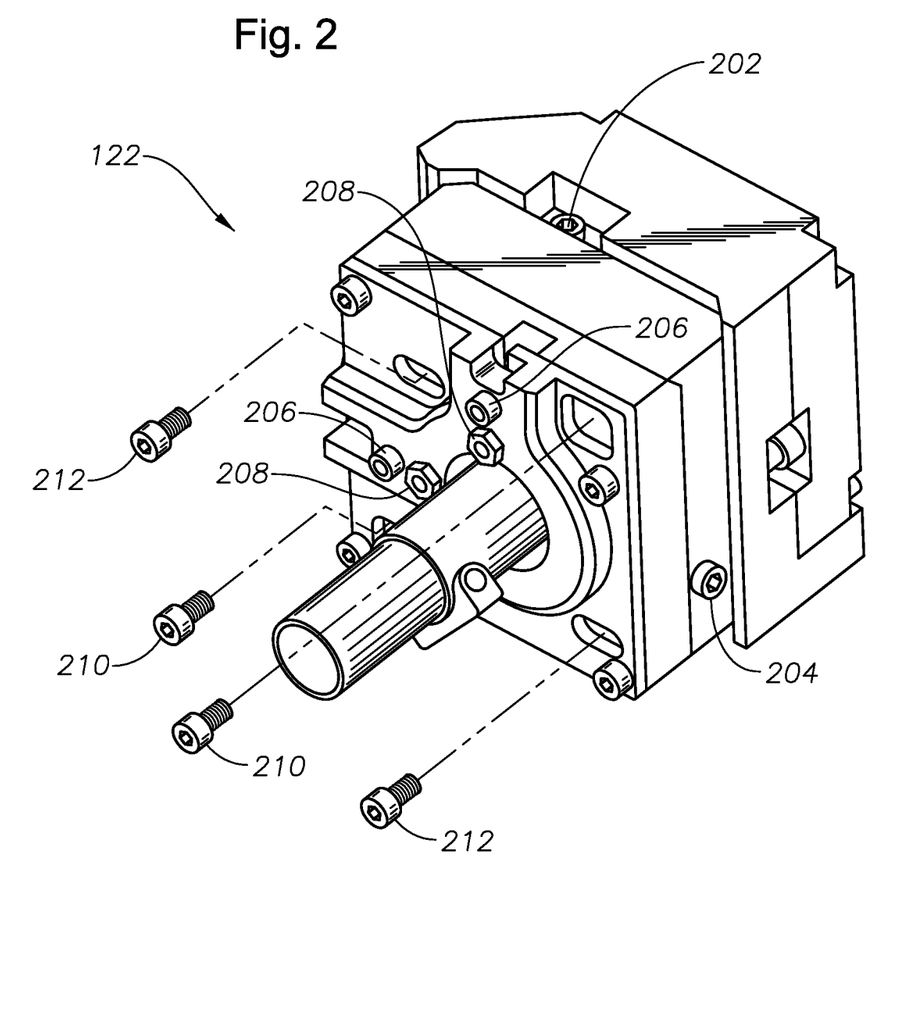
FIG. 2 provides an isometric view in more detail of the adjustable mount of FIG. 1 in accordance with an embodiment of the present disclosure.

FIG. 2 provides an isometric view in more detail of the adjustable mount 122 of FIG. 1 in accordance with an embodiment of the present disclosure. The adjustable mount may be locked down to base plate 112 and then relative to the lockdown there may be adjustments that may be made manually or through a control system through the use of servomotors. The adjustable mount 122 shown here includes vertical adjustment screws 202, horizontal adjustment screws 204. These allow the optical target to translate along a vertical and a horizontal axis. Additionally, the adjustable mount allows the optical target to rotate about these axes. This may be done through the use of rotational adjustment screws 206. The rotational adjustment screws allow rotation of the optical target about the vertical and the horizontal axes. Rotational lockdown nuts 208 allow the rotation to be fixed following adjustment. Similarly, vertical translation lockdown screws 210 and horizontal translation lockdown screws 212 allow the adjustable mount to be locked down relative to the vertical and horizontal axes.

Figure 3:
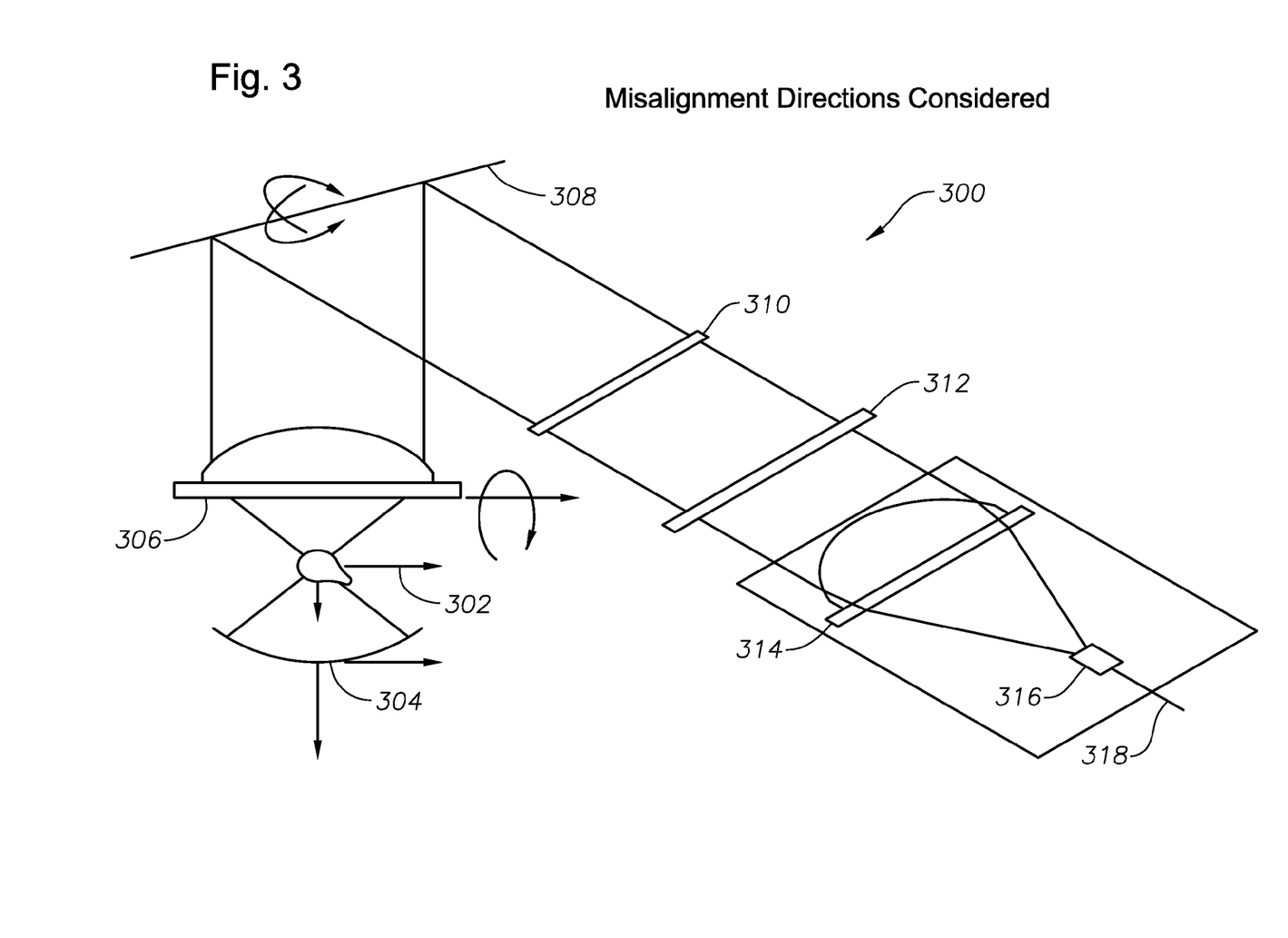
FIG. 3 depicts a fixed optical train in accordance with embodiment to the present disclosure.

FIG. 3 depicts a fixed optical train 300 in accordance with embodiment to the present disclosure. FIG. 3 shows the fixed components and their misalignment that can be compensated for by adjusting the Target. This optical train includes a light source 302, reflector 304, collimating lens 306, cold mirror 308, optical elements 310 and 312 such as filters, condensing lens 314, fiber optic port 316 and fiber optic 318. Embodiments of the present disclosure allow the positioning and alignment of fixed elements 302, 304, 306, 308, 310 and 312 to be tightly controlled during the manufacturing process and fixed relative to the optics bid. Then the adjustable target 320 having condensing lens 314, optical port 316 and fiber optic 318 may be translated about one or more optical axes and rotated about these axes. This allows for the misalignments of the various fixed elements to be compensated for with the adjustable optical target 320. This eliminates numerous potential corrections to be performed on the fixed elements as would normally occur in a pre-existing system.

Figure 4:
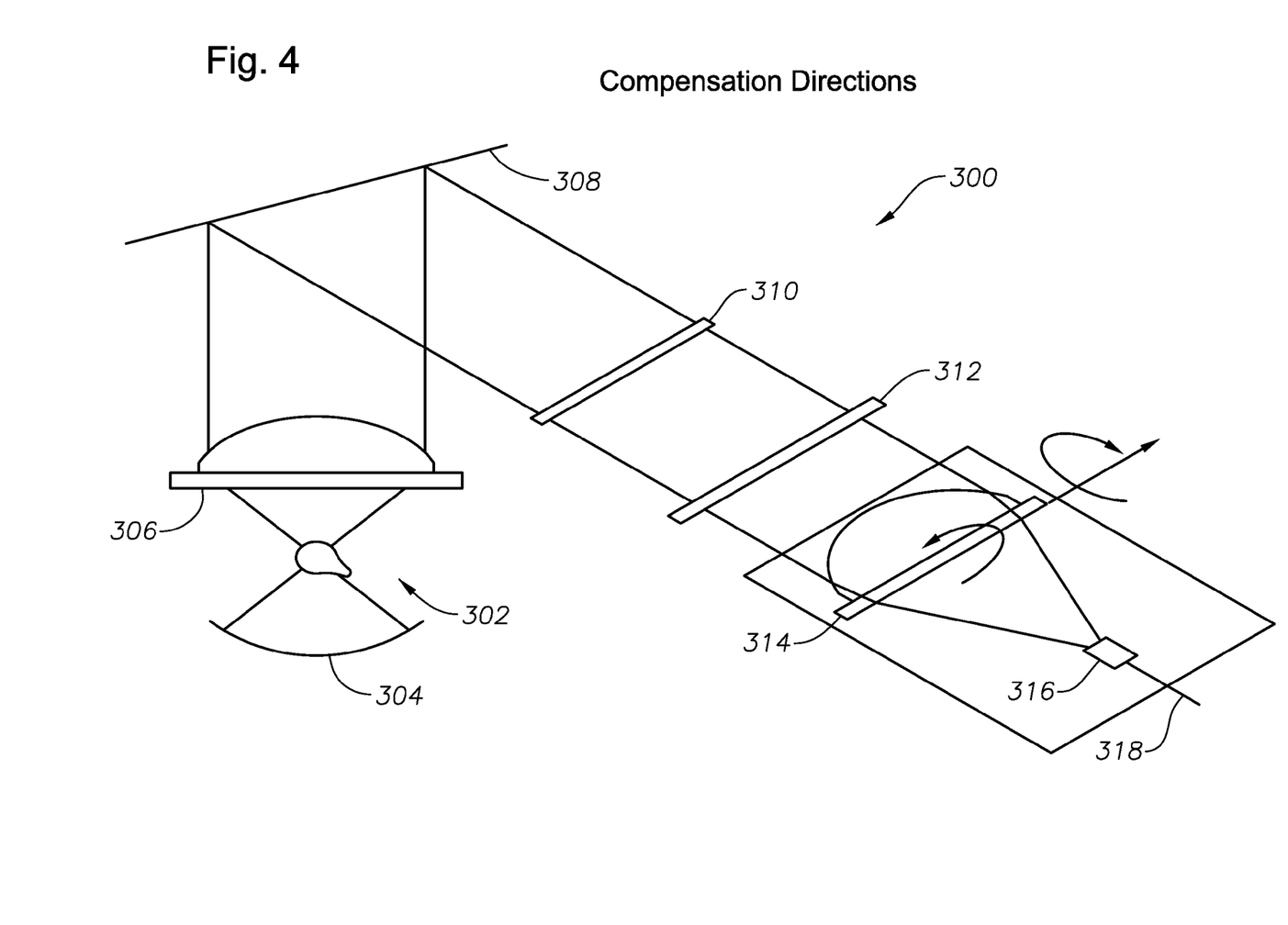
FIG. 4 again shows the fixed optical elements and optical train of fixed components with an adjustable optical target in accordance with embodiments with the present disclosure.

FIG. 4 again shows the fixed optical elements and optical train of fixed components with an adjustable optical target in accordance with embodiments with the present disclosure. In this case the rotation of condensing lens 314 about the vertical and horizontal axes is shown. In contrast FIG. 3 shows the translation about multiple axes of the adjustable optical target.

Figure 5:
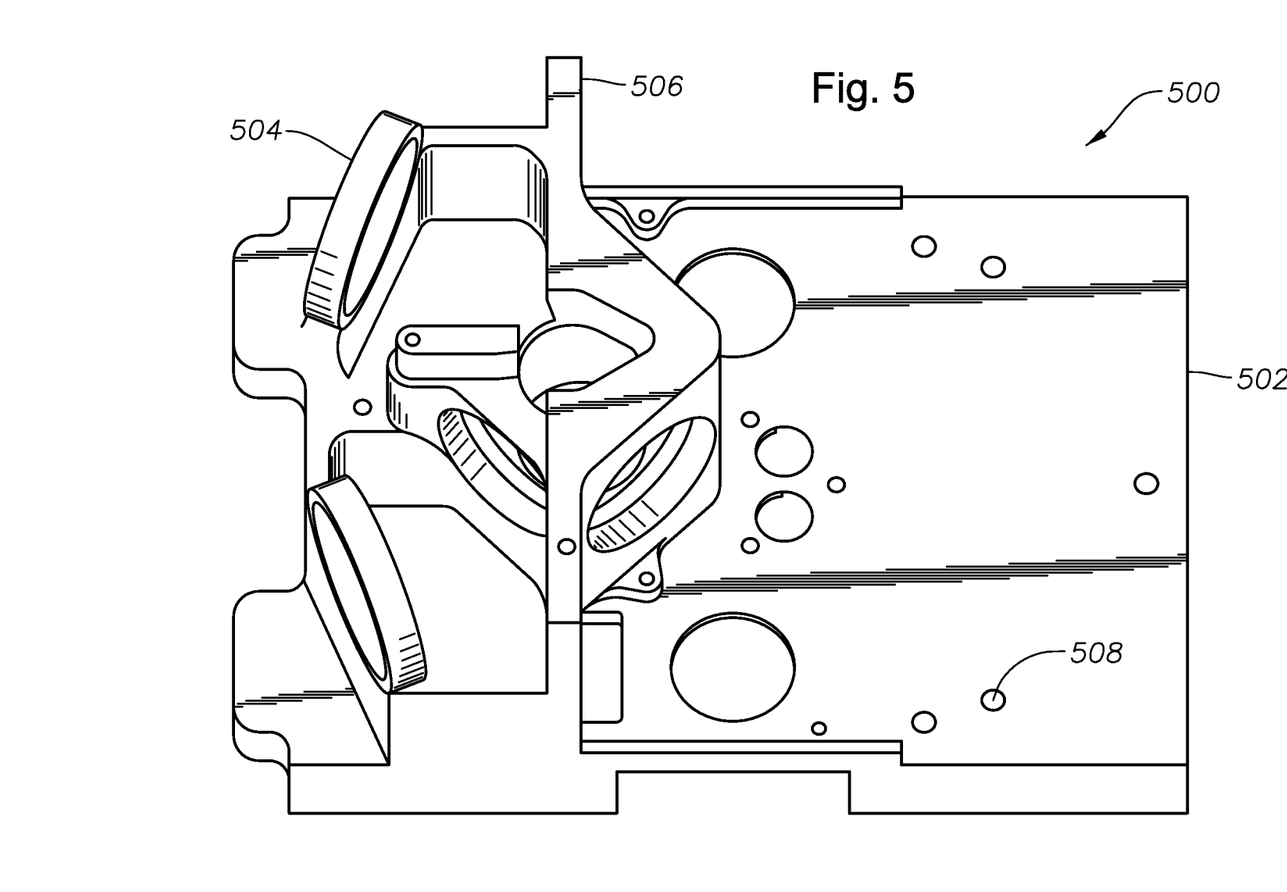
FIG. 5 depicts an embodiment of an optical bed in accordance with embodiments of the present invention.

FIG. 5 depicts an embodiment of an optical bed 500 in accordance with embodiments of the present invention. Optical bed 500 includes a base plate 502, various brackets 504 and an optical block 506. An optical block 506, screw holes 508 operable to receive the adjustable mount as well as an area for electronics such an electronic ballast or control system. The optical bed 500 shown here is integrally manufactured from a single piece of material. This eliminates potential problems associated with diverse coefficients of thermal expansion that can cause the path of the light generated to be distorted. The lamp may be located in the optical block 506 with collimating lenses and reflectors located in front and behind the lamp respectively. The collimated light exiting the collimating lens may be reflected by a cold mirror potentially located within brackets 504 and directed to the right towards the adjustable mount.

Figure 6:
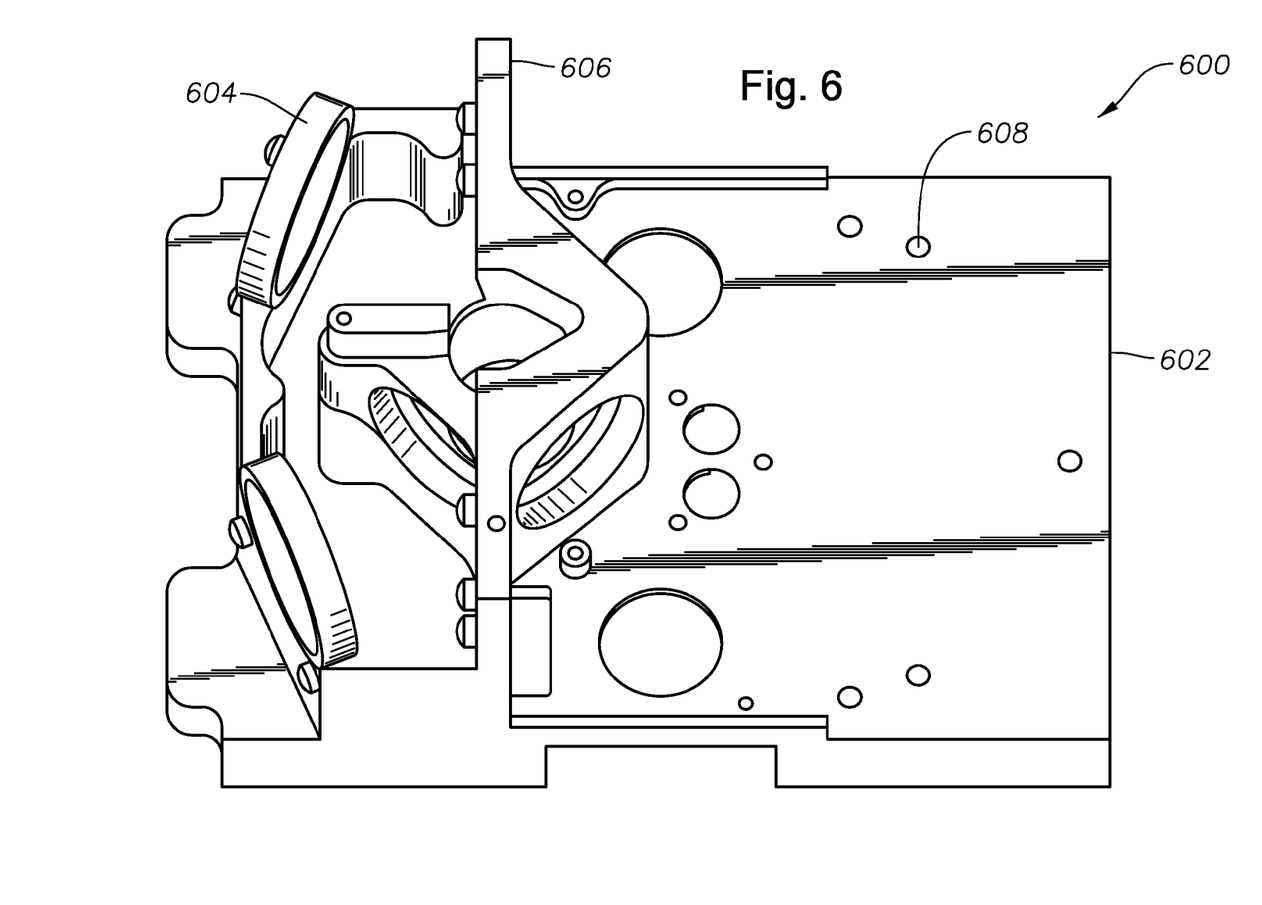
FIG. 6 depicts another embodiment of an optical bed in accordant optical bed in accordance with embodiments of the present invention.
Figure 7:
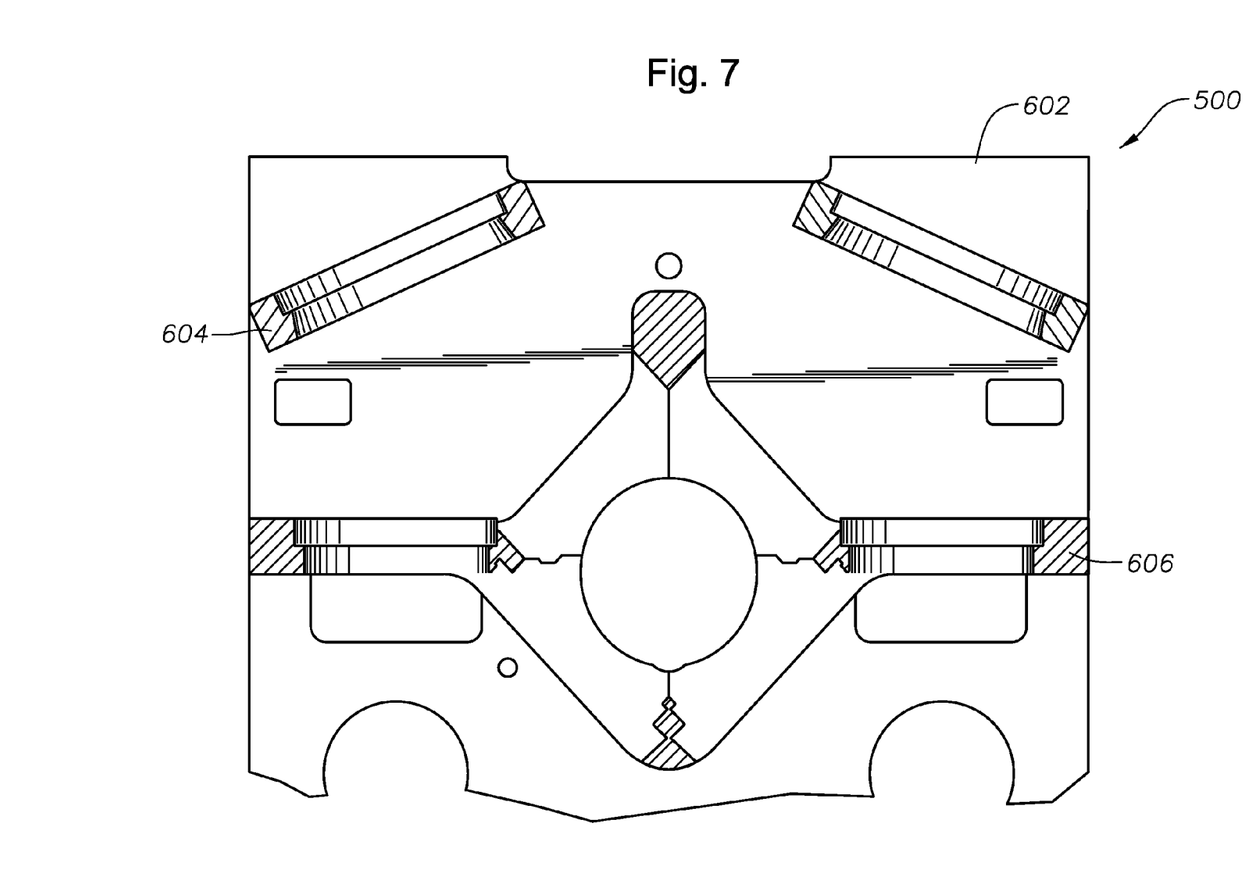
FIGS. 7 and 8 provide top down cross sections of an optical bed in accordance with embodiments of the present invention.
Figure 8:
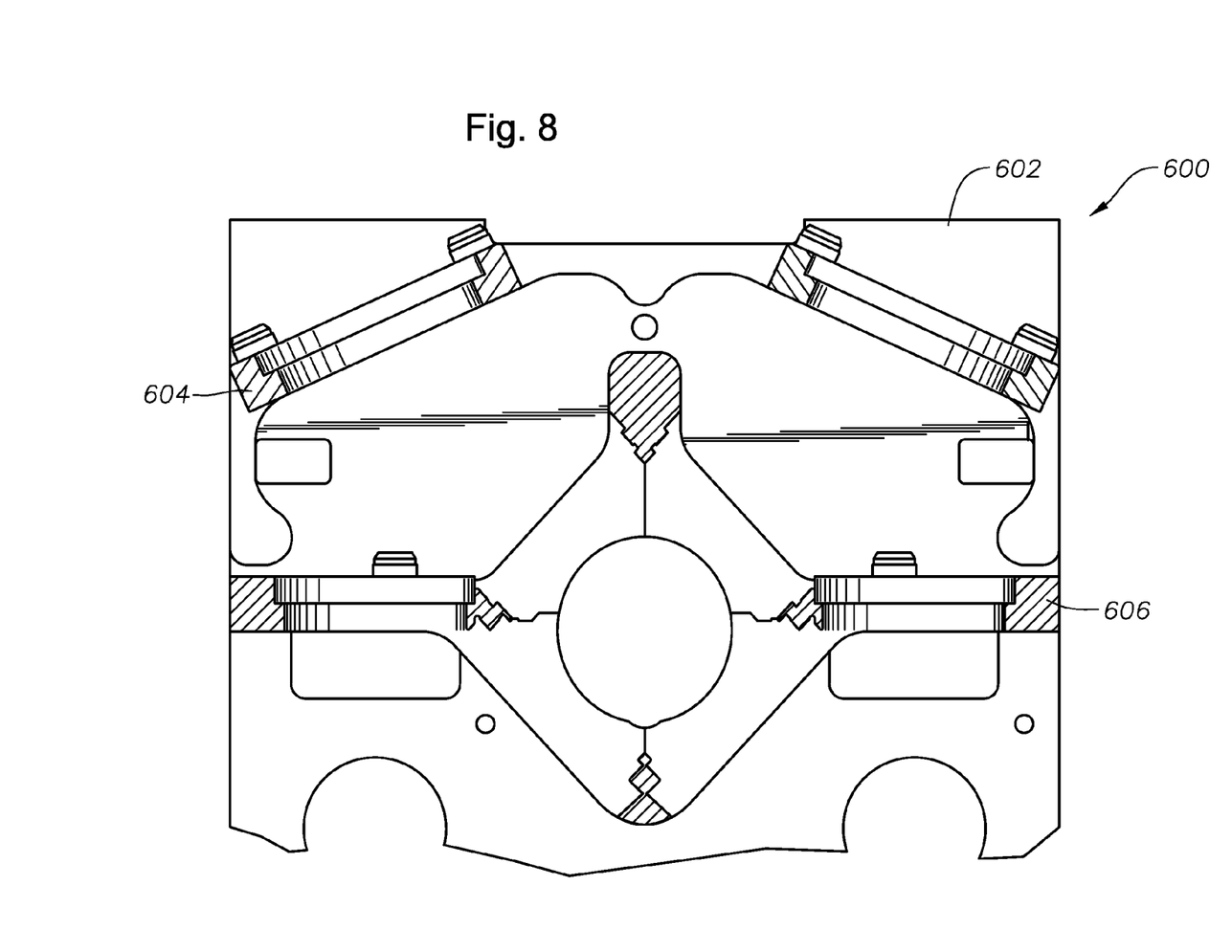

FIG. 6 depicts another embodiment of an optical bed in accordant optical bed 600 in accordance with embodiments of the present invention. Like the optical bed presented in FIG. 5, optical bed 600 includes a base plate 602, mounting brackets 604, and an optical block 606. Unlike the optical bed provided in FIG. 5 the optical bed of FIG. 6 is not machined or manufactured from a single piece of material. This then requires tight tolerances associated with the optical block 606, mounting brackets 604 and bed 602. Where these items must be securely mounted in order to prevent misalignments of the delivered light caused by shifts between the optical bed and the various optical elements. FIGS. 7 and 8 provide top down cross-sections of optical beds 500 and 600 respectively.

Figure 9:
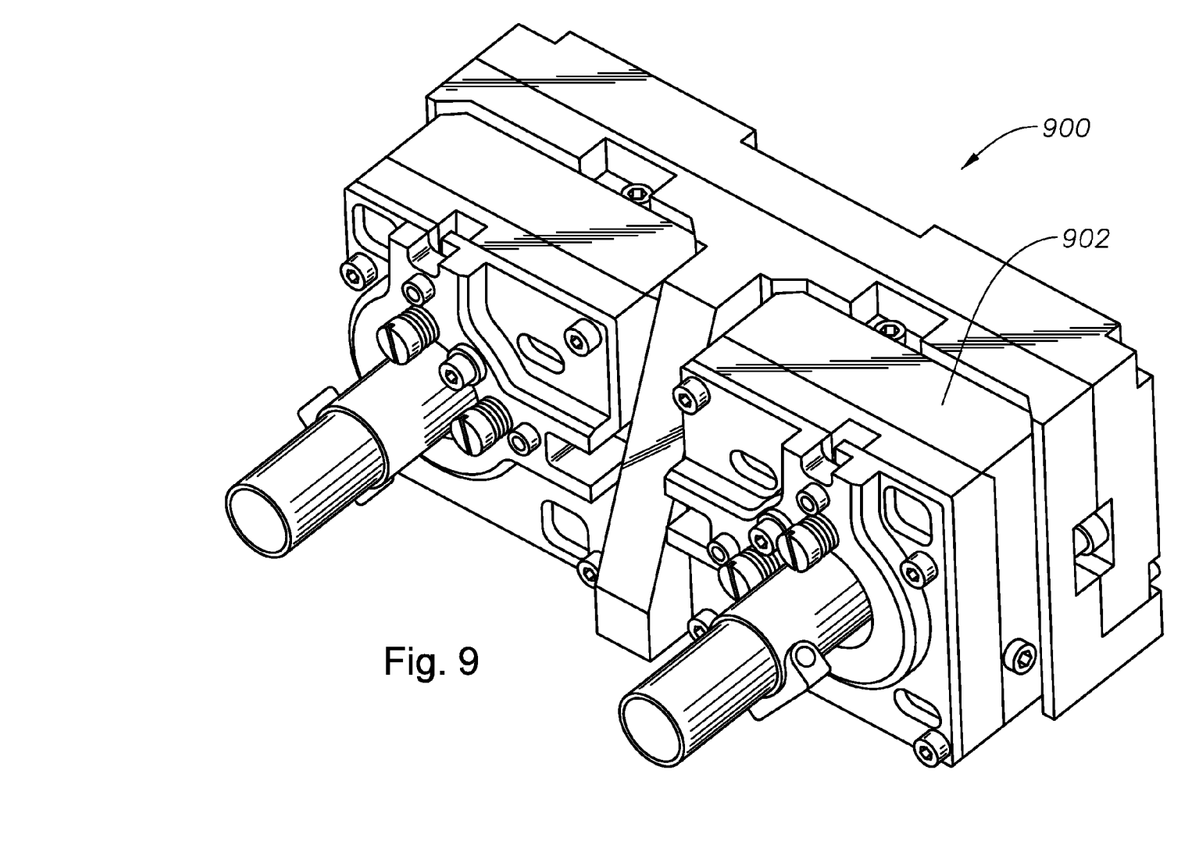
FIG. 9 provides an isometric view of an adjustable mount that may be mounted on an optical bed in accordance with embodiments of the present disclosure.

FIG. 9 provides an isometric view of an adjustable mount 900 that may be mounted on an optical bed in accordance with embodiments of the present disclosure. Adjustable mount 900 is operable to receive optical targets 902. These optical targets may include a condensing lens operable to focus the light generated such that the light may be provided to an optical fiber coupled to the condensing lens with an optical port. As previously described the adjustable mount 900 receives the optical targets which may be where the adjustable mounts allow for the optical targets to be translated in one or more axes such as a horizontal, vertical or longitudinal axes as well as rotated about the horizontal and the vertical axes.

Figure 10:
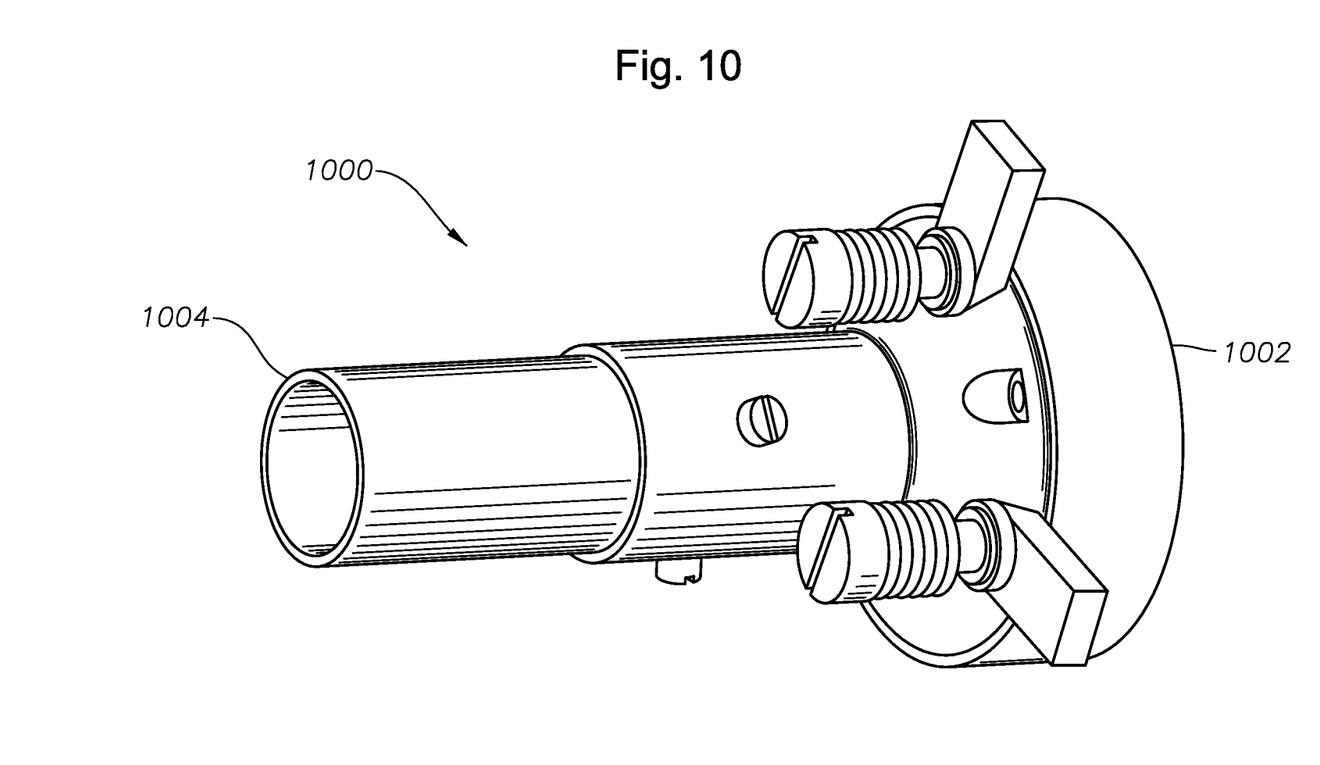
FIG. 10 depicts an optical port in accordance with embodiments of the present disclosure.
Figure 11:
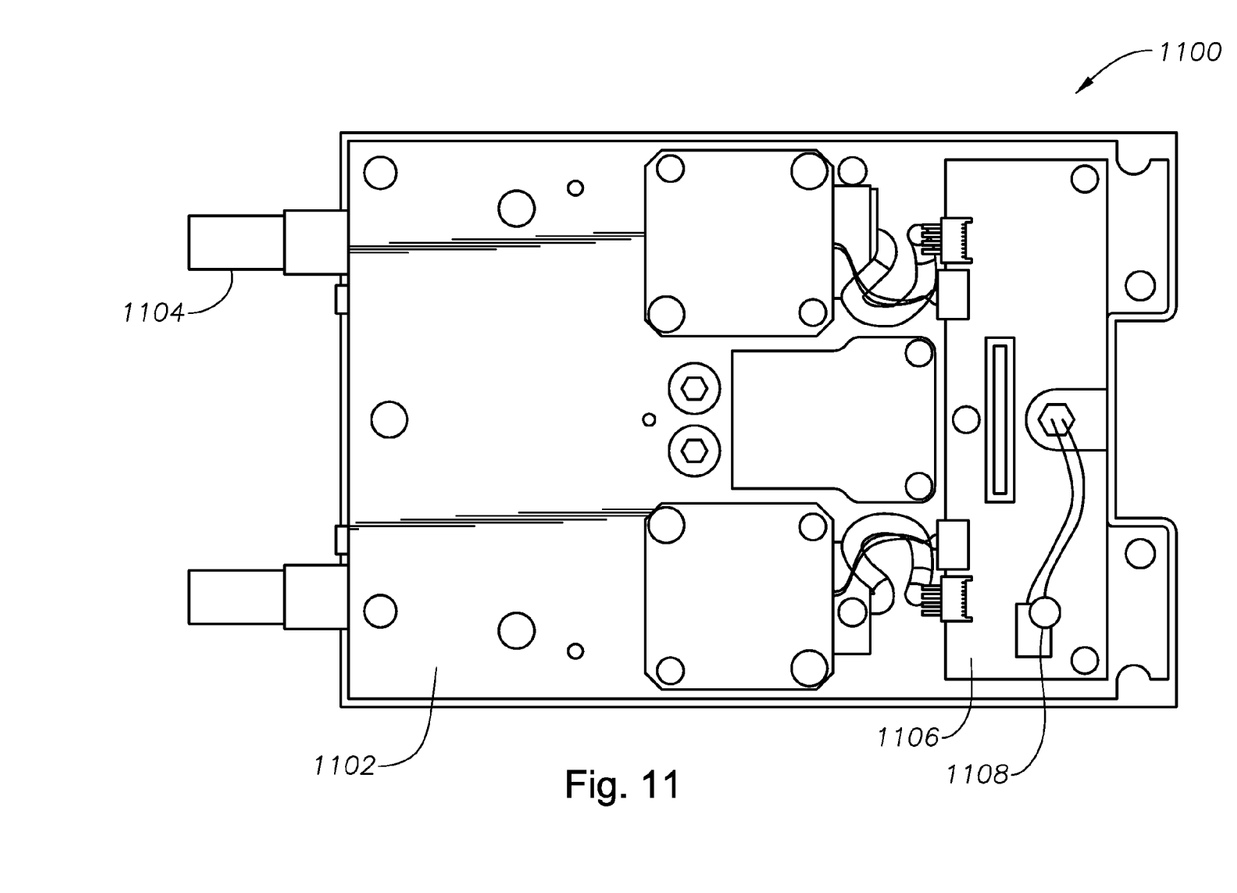
FIG. 11 provides a bottom side view of the optical system in accordance with embodiments of the present disclosure.

FIG. 10 depicts an optical port 1000 in which a condensing lens may be mounted at proximal end 1002 while distal end 1004 is operable to receive an optical fiber that may then be optically coupled to the condensing lens. Adjustment screws 1006 allow the adjustment of the optical port 1000 with respect to the optical bed FIG. 11 provides a bottom side view of the optical system 1100 in accordance with embodiments of the present disclosure. This bottom side view of the optical system 1100 shows a base plate 1102, optical ports 1004 but does not readily depict the optical elements which may be more easily seen from a top or side view. Rather this view additionally depicts the use of electronics 1106 and sensors 1108 within the optical system. The electronics may include a control system as well as various sensors. This may take the form of an electronic ballast 1106 which may provide controls to certain optical components as well as conditioning power to be provided to the light source or lamp within the optical bed. A thermistor or other sensor 1108 may be incorporated and physically coupled to the optical bed 1100. This allows an input to be provided from the thermistor to the control system within the electronic ballast such that the adjustable mount may translate and rotate the optical target automatically in response to environmental changes to which the optical bed is exposed. This further enhances the ability of a system using this optical bed to remain aligned during changing conditions.

Figure 12:
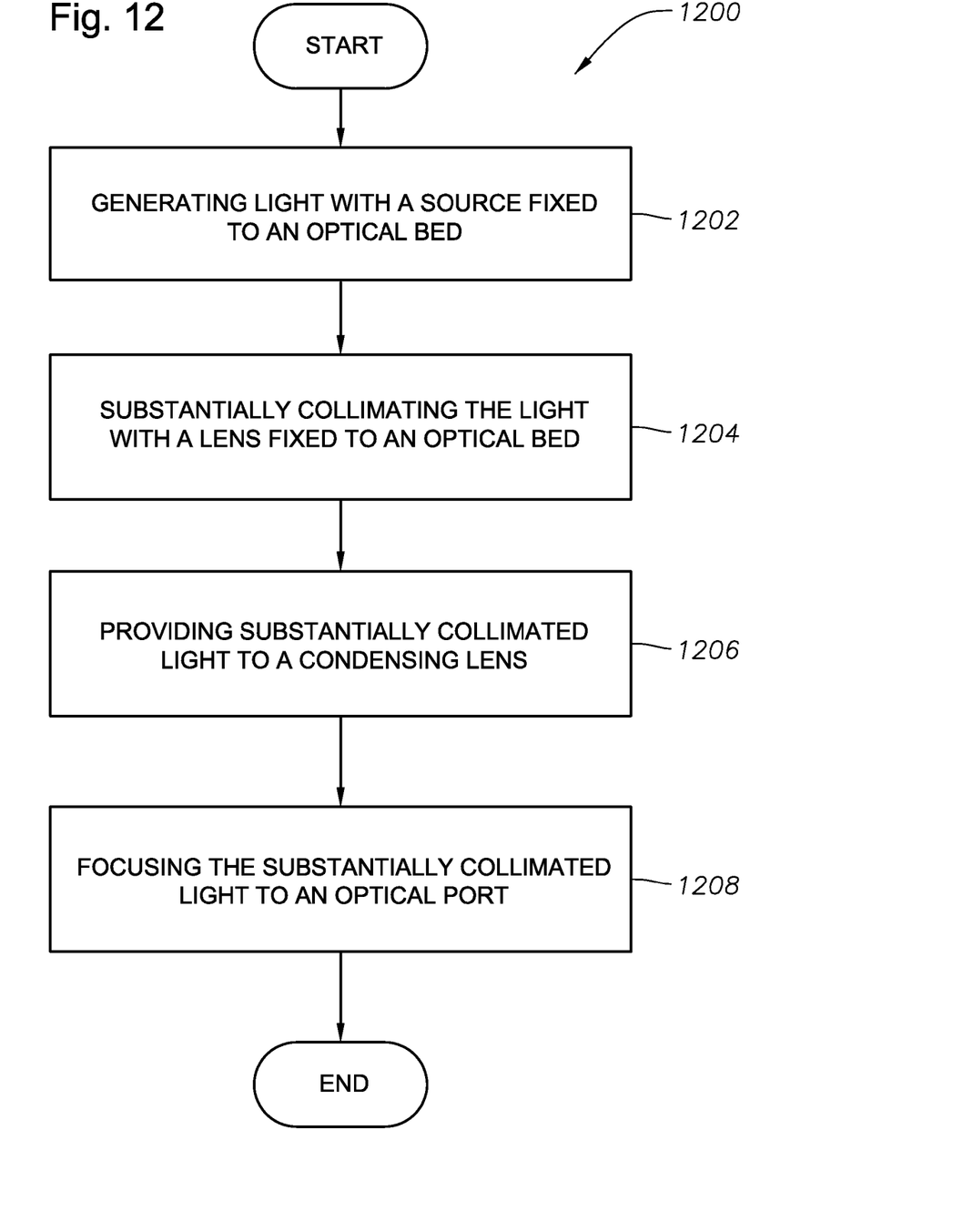
FIG. 12 provides a logic flow diagram associated with a method of generating an input to a fiber optic or optical fiber in accordance with embodiments of the present disclosure.

FIG. 12 provides a logic flow diagram associated with a method of generating an input to a fiber optic or optical fiber in accordance with embodiments of the present disclosure. Operations 1200 begin with block 1202 where light is first generated with a light source wherein the light source is fixed to an optics bed. A collimating lens which is also fixed to the optics bed substantially collimates the light in block 1204. The light is then provided to a condensing lens in block 1206. The condensing lens focuses or optically couples the substantially collimated light to an optical port operable to receive an optical fiber in block 1208. The condensing lens may be adjustably mounted to the optics bed. This may be done so with an adjustable mount wherein the mount allows the condensing lens to translate and rotate about one or more axes.

In summary, embodiments provide a fiber optic illuminator. This fiber optic illuminator includes at a minimum an optics bed, a light source, a collimating lens, and a condensing lens. The light source is mounted in a fixed position with respect to the optics bed. The light source produces light. The collimating lens which is also mounted in a fixed position with respect to the optics bed substantially collimates at least a portion of the light output of the light source. A condensing lens receives the substantially collimated light output and focuses or condenses the collimated light output so that it may be optically coupled to an optical fiber. The condensing lens may be mounted on an adjustable mount. This adjustable mount may allow the condensing lens to translate along one or more axes and rotate about the one or more axes. The tolerances of the fixed optical elements i.e. light source and collimating lens allow the fixed optical elements to be positioned with a minimal amount of variation where the variation is determined by manufacturing tolerances associated with these individual elements and their mounts and couple them to the optics bed.

The advantage of a fixed optical system with adjustable target is a vast reduction in the number of adjustments necessary to align the optical system. As described above, a simple optical train could require 25 adjustments to properly align the system. By fixing the location of each of the optical members allowing them to vary only by the manufacturing tolerance of their locating components, and adjusting the location and angle of target component, these 25 adjustments can be reduced to 4. This is an improvement in several ways;

(1) Reduction in the time needed to align the system;
(2) Reduction in the number of parts used in the assembly, since parts are needed for only 4 adjustable stages as compared to 25.
(3) Increase in reliability due to less mechanisms to fall out of adjustment
(4) Reduction it the overall package size due to less adjustable stages.

The present disclosure is illustrated herein by example, and various modifications may be made by a person of ordinary skill in the art. Although the present disclosure is described in detail, it should be understood that various changes, substitutions and alterations can be made hereto without departing from the spirit and scope of the disclosure as described.

What is claimed is:

1. A fiber optic illuminator comprising:
    a plurality of fixed optical elements, comprising a light source and a collimating lens;
    an optics bed, the plurality of fixed optical elements mounted in fixed positions with respect to the optics bed; and
    an adjustable condensing lens-port assembly attached to the optics bed, the adjustable condensing lens-port assembly,
        operable to accept an optical fiber,
        adjustable for translation along at least one axis, and
        adjustable for rotation about the at least one axis;
    wherein
    the condensing lens is positioned to focus collimated light from the collimating lens onto the optical fiber, wherein the optical fiber is coupled to the condensing lens-port assembly.

2. The fiber optic illuminator of claim 1, the plurality of fixed optical elements further comprising elements selected from the group of:
    an image reflector; and
    a cold mirror.

3. The fiber optic illuminator of claim 1, the optics bed comprising:
    a base plate; and
    at least one optical element bracket, the at least one optical element bracket fixed to the base plate.

4. The fiber optic illuminator of claim 1, the optics bed comprising:
    a base plate;
    at least one optical element bracket, the at least one optical element bracket fixed to the base plate; and
    at least one optical block, the at least one optical block fixed to the base plate.

5. The fiber optic illuminator of claim 1, the optics bed comprising:
    a base plate;
    at least one optical element bracket; and
    at least one optical block, the base plate, at least one optical element bracket, and at least one optical block manufactured integrally from a single block of material.

6. The fiber optic illuminator of claim 1, the adjustable condensing lens-port assembly:
    adjustable for translation along a plurality of axes; and
    adjustable for rotation about the plurality of axes.

* * * * *